United States Patent
Eckfeldt

[11] 3,980,543
[45] Sept. 14, 1976

[54] ELECTROCHEMICAL CELL STRUCTURE

[75] Inventor: Edgar L. Eckfeldt, Ambler, Pa.

[73] Assignee: Leeds & Northrup Company, North Wales, Pa.

[22] Filed: Dec. 4, 1974

[21] Appl. No.: 529,414

[52] U.S. Cl. .......................... 204/195 S; 204/1 T; 204/195 R; 429/30; 429/104
[51] Int. Cl.² ................ G01N 27/46; H01M 27/16
[58] Field of Search .............. 204/1 T, 1 S, 195 R, 204/195 S; 136/86 R, 86 F, 153

[56] References Cited
UNITED STATES PATENTS

| | | | |
|---|---|---|---|
| 3,120,456 | 2/1964 | Broers | 136/86 F |
| 3,619,381 | 11/1971 | Fitterer | 204/195 S |
| 3,630,874 | 12/1971 | Olette et al. | 204/195 S |
| 3,642,599 | 2/1972 | Franz | 204/195 S |
| 3,867,312 | 2/1975 | Stephens | 252/463 |

*Primary Examiner* — T. Tung
*Attorney, Agent, or Firm* — Phil J. Moore; Raymond F. MacKay

[57] ABSTRACT

An assembly for insertion in a bath of molten material to form therewith an electrochemical cell for determining the concentration of a constituent of the bath. The assembly is of the type including a body structure of refractory material from which protrudes a first electrically conductive element providing means for establishing an electrical connection with the bath and a reference electrode structure separated from the bath by means of a rigid electrolyte material. Reference electrode structures of this general type may be comprised of a closed end tube of electrolyte material or a tube of electrically non-conductive refractory material having a pellet of electrolyte material closing the immersion end thereof to separate the material of the bath from the means establishing a reference potential. In accordance with one form of applicant's invention the rigid electrolyte material is comprised of a component which is ionically conductive at the operating temperature of the cell which component may be supported within a passage of capillary dimensions between surfaces, or in interstices or on the surface of particles of supporting means having a melting point which is above the operating temperature of the cell. In most instances the ionically conductive component will tend to soften or melt at a temperature below the operating temperature of the cell but be retained in the space of capillary dimensions or in interstices or on the surface of particles of the supporting means which remains solid at cell operating temperature.

10 Claims, 7 Drawing Figures

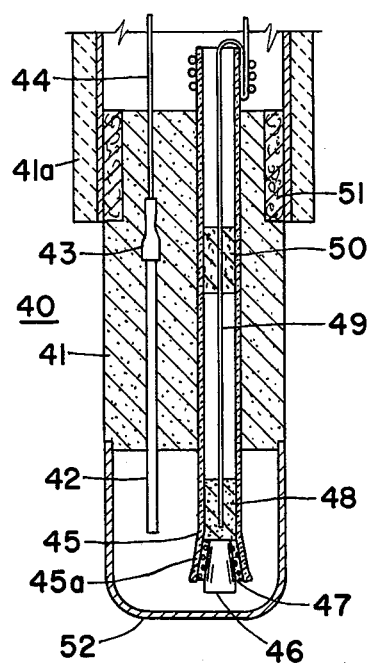
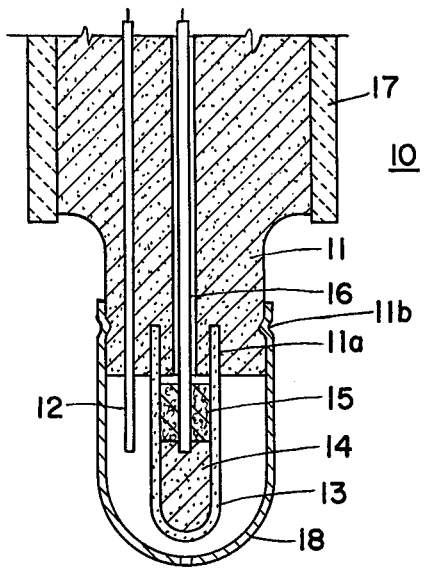
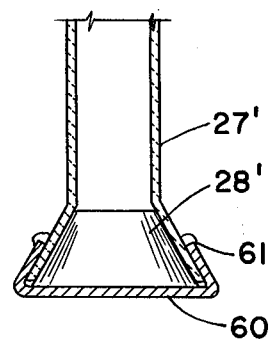
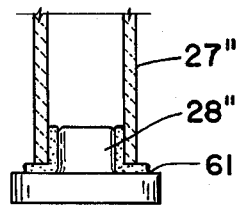
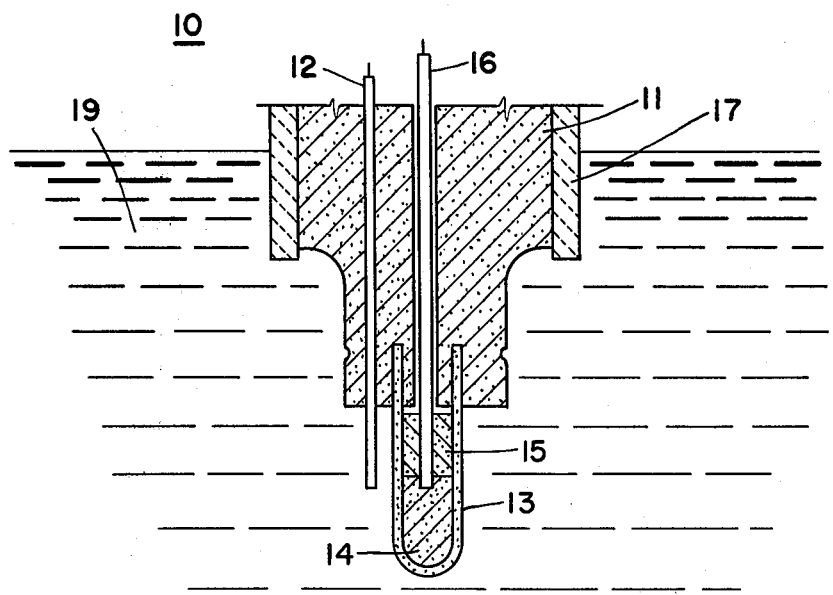

ELECTROCHEMICAL CELL STRUCTURE

BACKGROUND OF THE INVENTION

1. Field of the Invention

Applicant's invention is used with a molten material to form an electrolyte cell. Such a cell is sometimes referred to as a galvanic cell or an electrochemical concentration cell. Devices of the foregoing type are variously classified in the United States Patent Office in official subclasses entitled, "Batteries, Electrolytes; or Chemistry, Electrical and Wave Energy, Processes and Products, Electrolysis, Analysis and Testing; or Chemistry, Electrical and Wave Energy, Apparatus, Electrolytic, Analysis and Testing, Solid Electrolyte; or Electricity, Measuring and Testing; Determining Non-Electrical Properties by Measuring Electrical Properties."

2. Description of the Prior Art

During the past several years considerable time and money has been expended by many individuals in an effort quickly to determine and/or control the amount of one or more constituents in a bath of molten material by means of techniques utilizing a galvanic cell, i.e., an electrolytic cell. Much has been accomplished towards the development of electrode assemblies suitable for insertion into a bath of molten metal such as liquid aluminum, copper, iron, or steel to form therewith an electrolytic cell for determination of the concentration of a constituent, frequently oxygen. The state of the art as of 1968 and a brief historical review of developments relating to oxygen determination is set forth in a paper prepared for presentation at the 76th General Meeting of American Iron and Steel Institute, in New York, May 23, 1968, by E. T. Turkdogan and R. E. Fruehan entitled "Rapid Oxygen Determination in Liquid Steel." A copy of the paper is available upon request from the American Iron and Steel Institute, 150 E. 42nd Street, New York, New York 10017.

In the Turkdogan et al. paper there is disclosed a disposable immersion type, plug-in unit including a reference electrode assembly for forming an electrolytic cell when immersed in liquid steel. The plug-in electrical connections are like those used in disposable, i.e., expendable immersion thermocouples of the plug-in type disclosed in U.S. Pat. Nos. 2,999,121—H. G. Mead; 3,024,295—P. J. Moore; and 3,048,642—K. B. Parker, Jr. Expendable thermocouples are well known to those skilled in the arts wherein the temperature of a bath of molten material is to be measured and particularly to those skilled in the arts of producing steel and cast iron. Thermocouples of this type are plugged into a receptacle at the immersion end of a manipulator, sometimes referred to as a holder or a lance, which established an electrical connection to a measuring circuit which generally includes a self-balancing potentiometer recorder.

U.S. Pat. No. 3,785,947—W. H. Baldwin et al. also discloses a plug-in immersion assembly which when immersed in a molten metal forms an electrolytic cell for measuring oxygen in a bath of molten steel.

In the processing of steel a plug-in unit including structure for immersion in a molten bath to form an electrolytic cell for the determination of oxygen as disclosed in the Turkdogan et al article and the Baldwin et al. patent has been found very convenient to use. A similar construction for obtaining a measure of other constituents in steel or other molten materials would likewise have great utility, however, when the temperature of the molten material is high relative to the melting temperature of constituent-responsive electrolyte materials such, for example, as for the determination of manganese in molten steel, it has heretofore been considered impossible to make a structure suitable for insertion in the bath of molten material to form therewith an electrolytic cell.

The principles of electrochemical cells are well known to those skilled in the art and are set forth in greater detail in text books, the Turkdogan et al. paper, and the references listed in the bibliography thereof. Since the principles per se are not applicant's invention they will be treated only briefly herein.

An electrochemical cell may be schematically represented generically in a table as follows:

Table I

| 1 | 2 | 3 | 4 | |
|---|---|---|---|---|
| (A) Electronic conductor | (B) Molten sample containing constituent to be measured | (C) Constituent responsive material i.e. Electrolyte Material | (D) Reference potential producing material | (F) Electronic conductor |

In the above representation the substances comprising the cell are symbolized by letters. The numbered vertical lines represent phase boundaries and hence sources of e.m.f. For sake of simplicity the electronic conductors A and F are assumed to be solids. The molten sample B is assumed to be liquid. The reference potential producing material D depending upon the constituent to be measured, may be a solid, liquid, or gas. The constituent-responsive material, i.e., electrolyte material C may be either a solid or liquid and will be chosen for its ability to develop a thermodynamically reversible e.m.f., i.e., an interfacial voltage with respect to the activity (concentration) of the constituent of interest at either interface or phase boundary 2 or 3. Solid or liquid conditions other than those assumed if kept constant will not change the basic theory as presented. Constancy, or approximate constancy, of temperature of the cell is assumed in considering the e.m.f.'s at the interfaces 1 through 4.

As disclosed in an article entitled "On the Activities of Coexisting Elements in Molten Iron. III The Activity of Mn in Molten Fe-Mn Alloy" by Koji Sanbongi and Masayasu Ohtani, Science Reports of the Research Institute, Tohoku Univ., Sendai, Series A, Vol. 7 pp. 204–209 (1955) the Mn content in iron has been measured using an electrolytic concentration cell wherein the components corresponding to B, C, and D of the above table comprised liquids contained in a crucible of special shape. The cell is represented by the following table:

TABLE II

| 1 | 2 | 3 | 4 |

TABLE II-continued

| (A) W | (B) ⊖Fe—Mn | (C) SiO—MnO—MgO—CaO | (D) Mn ⊖ | (F) W |
|---|---|---|---|---|
|  |  |  |  |  |

That is to say molten Mn was used as the standard electrode to provide a reference potential, molten Fe—Mn alloys containing various amounts of Mn constituted the other electrode and molten slag containing MnO was used as the intermediate electrolyte. A special crucible containing the molten materials was made of MgO and the synthetic slag was obtained by melting high purity MnO, $SiO_2$, and CaO in an MgO or $Al_2O_3$ crucible and pouring it into the special crucible. Tungsten wires having ends extending into the molten Fe—Mn alloy and the molten Mn provided electrical connections for the cell and the e.m.f. between them was measured with a potentiometer.

While the cell above described is satisfactory for the measurement of Mn in Fe—Mn alloys it would appear to be limited in its use to laboratory type operations. There is no apparent way of employing it for insertion into a bath of molten material such as that contained within a furnace or ladle in the manner described by Turkdogan et al.

While theoretically any of many presumably stable manganese compounds such as MnO, $Mn_2P_2O_7$; $Mn_2SiO_4$; and $MnSiO_3$; for example, would appear to be suitable materials to develop a potentiometric signal, that is, a thermodynamically reversible e.m.f. with respect to the manganese activity (concentration) at either interface, i.e., phase boundary 2 or 3, it has not heretofore been known how to employ such materials in a structure which can be immersed in a bath of molten metal at temperatures as high as the temperature of molten steel.

Applicant has discovered a way whereby it becomes possible to utilize in an assembly for insertion in a bath of molten material constituent-responsive materials which are ionically conductive and/or may melt or soften at a temperature below the operating temperature of an electrolytic cell.

SUMMARY OF THE INVENTION

It is an object of applicant's invention to provide an assembly for insertion in a bath of molten material to form therewith an electrochemical cell for determining the concentration of a constituent of the bath of molten material. The assembly includes a first electrically conductive element providing means for establishing an electrical connection with the bath. The assembly also includes a reference electrode structure including means establishing a reference potential. A constituent-responsive electrolyte material is interposed between the bath and the means establishing a reference potential to establish a partition therebetween. There is a second electrically conductive element providing means for establishing an electrical connection with the means establishing a reference potential and the electrolyte material. The electrolyte material is believed novel in that it comprises a component which is ionically conductive at the operating temperature of the cell and retains its structural integrity to withstand the hydrostatic forces imposed when the assembly is plunged into a bath of molten material. The electrolyte material is supported within interstices or on the surface of particles of a porous supporting component having a melting point which is above the operating temperature of the cell. The voltage measured between the first and second conductors is indicative of the concentration of the constituent to be determined.

More specifically it is an object to provide an assembly of the above type for determining the manganese content of a bath of molten metal, such as steel, wherein the ionically conductive component is a compound of manganese and the porous supporting component is of a material such as silica, alumina, beryllia, or zirconium silicate having a melting point above that of the operating temperature of the cell.

It is further an object to provide an assembly of the above type wherein the electrolyte material comprises a fired mixture of materials containing as the ionically conductive component a material which melts or softens at a temperature below the operating temperature of the cell, supported on the porous component, having a melting point which is above the operating temperatures of the cell. This fired mixture may be comprised of 1 to 25 weight percent MnO mixed with $SiO_2$ having particles 200 to 350 mesh size before firing, and/or comprised of 7.4 weight percent MnO and 92.6 weight percent $SiO_2$ before firing.

It is also an object of Applicant's invention to provide an assembly as above described wherein the mixture is comprised of $MnSiO_3$ and $ZrSiO_4$ before firing, or a mixture comprised of $MnSiO_3$ and $Al_2O_3$ before firing.

It is still further an object to provide an assembly of the type described above wherein the porous supporting material supporting the ionically conductive material is in the form of a tube closed at the immersion end thereof and with the other end of the tube being sealed into a body member. The tube contains the means establishing a reference potential and the second electrically conductive element extends into the tube into electrical connection with the means establishing a reference potential and the ionically conductive material. Instead of a tube the porous supporting material supporting the ionically conductive material may be in the form of a closure member in a wall of a vessel made of refractory material. The vessel may be a tube of refractory material with an end closure member in the form of a pellet.

It is a specific object of applicant's invention to provide an assembly for insertion in a bath of molten material to form therewith an electrochemical cell for determining the manganese content of the bath wherein the electrolyte material includes a component comprised of a compound of manganese and the means establishing a reference potential is comprised of metallic manganese which may additionally include some manganous silicate.

It is also an object of applicant's invention to provide an assembly for insertion into a bath of molten steel to form therewith a concentration cell for determining the concentration of manganese in the bath. The assembly comprises a body structure capable of withstanding insertion in the bath for a length of time necessary to obtain a measurement. There is a first electrically conductive element of refractory material having one end protruding from the body structure for contact with the bath and an end thereof inside the body structure electrically connected to means for connecting this element to a measuring instrument. The body structure also has a closed end tubular structure of refractory material projecting therefrom with at least a portion of the projecting end of the tubular structure being comprised of electrolyte material having an ionically conductive component which melts or softens at a temperature lower than the melting temperature of steel. The ionically conductive component is supported by a porous supporting component having a melting point which is above the temperature of molten steel. A manganese reference material is contained within the tubular structure in electrically conductive relation with the electrolyte material and there is a second electrically conductive element extending within the tubular structure and with an end thereof in electrically conductive relation with the reference material and the electrolyte material. The other end of the second electrically conductive element is electrically connected within the body structure to means for connecting the second electrically conductive element to a measuring instrument. Means is also provided for preventing the ingress of molten steel into the body structure. Additionally, the assembly may include heat destructible means supported by the body structure in position to protect parts of the assembly prior to and during insertion of the assembly through any slag layer existent on a bath of molten steel.

It is likewise an object of applicant's invention to provide a method of making an assembly for insertion into a bath of molten steel to form therewith a concentration cell for measuring the amount of manganese in the bath. The method comprises the steps of preparing a mixture of controlled particle size containing a manganese compound combined with a refractory material, treating a quantity of the mixture with a quantity of temporary binding material to form a powder, placing a quantity of the powder in a die and applying pressure to form a pellet, heat treating the pellet under a reducing atmosphere, fastening the pellet in a tube of refractory material to form a closure at an immersion end thereof, mounting in a body structure a rod of refractory metal and the tube with immersion ends thereof projecting from the body structure, inserting an electrically conductive element and a reference material into the tube and affixing electrically conductive means to the rod of refractory metal and the electrically conductive element to provide means for connecting the assembly to a measuring instrument.

It is also an object of applicant's invention to provide an assembly for insertion in a bath of molten steel to form therewith an electrochemical cell for determining the concentration of manganese in the bath. The assembly includes a reference electrode structure comprised of means providing a rigid partition between the bath and a material establishing a reference potential for manganese contained by the partition with at least a part of the partition including manganese responsive material.

Also it is an object of applicant's invention to provide an assembly for insertion in a bath of molten material to form therewith an electrochemical cell for determining the concentration of a constituent in the bath wherein the assembly includes a reference electrode structure comprised of tubular means closed at the immersion end thereof with a pellet containing a constituent responsive material with the tubular means and pellet being constructed and arranged so that upon immersion of the assembly into the bath the hydraulic head of the molten material of the bath will apply a force upon the pellet in a direction tending to effect engagement between the pellet and the tubular mens.

In one modification the tubular means has an outwardly flared portion at its immersion end and the pellet has a conical outer wall portion for mating engagement with the flared portion of the tubular means. In another modification the tubular means has a straight portion at its immersion end and the pellet has a portion of lesser cross section for reception in the immersion end of the tubular means and a portion of greater cross section forming a shoulder for butting engagement with the immersion end of the tubular means.

BRIEF DESCRIPTION OF THE DRAWINGS

For a better understanding of applicant's invention and the objects thereof the following description and claims should be read with reference to the accompanying drawings wherein:

FIG. 1 is a side elevation partly in section of the lower end of an assembly according to applicant's invention for insertion in a bath of molten material, FIG. 2 shows the assembly of FIG. 1 inserted in a bath of molten material, FIG. 5 is a side elevation of a modification of the assembly of FIG. 3, FIG. 6 is a side elevation on an enlarged scale showing an alternate construction for tube 27 of FIG. 3, and FIG. 7 is a side elevation on an enlarged scale of another form of construction for tube 27 of FIG. 3.

DETAILED DESCRIPTION OF THE INVENTION

Figure 3:
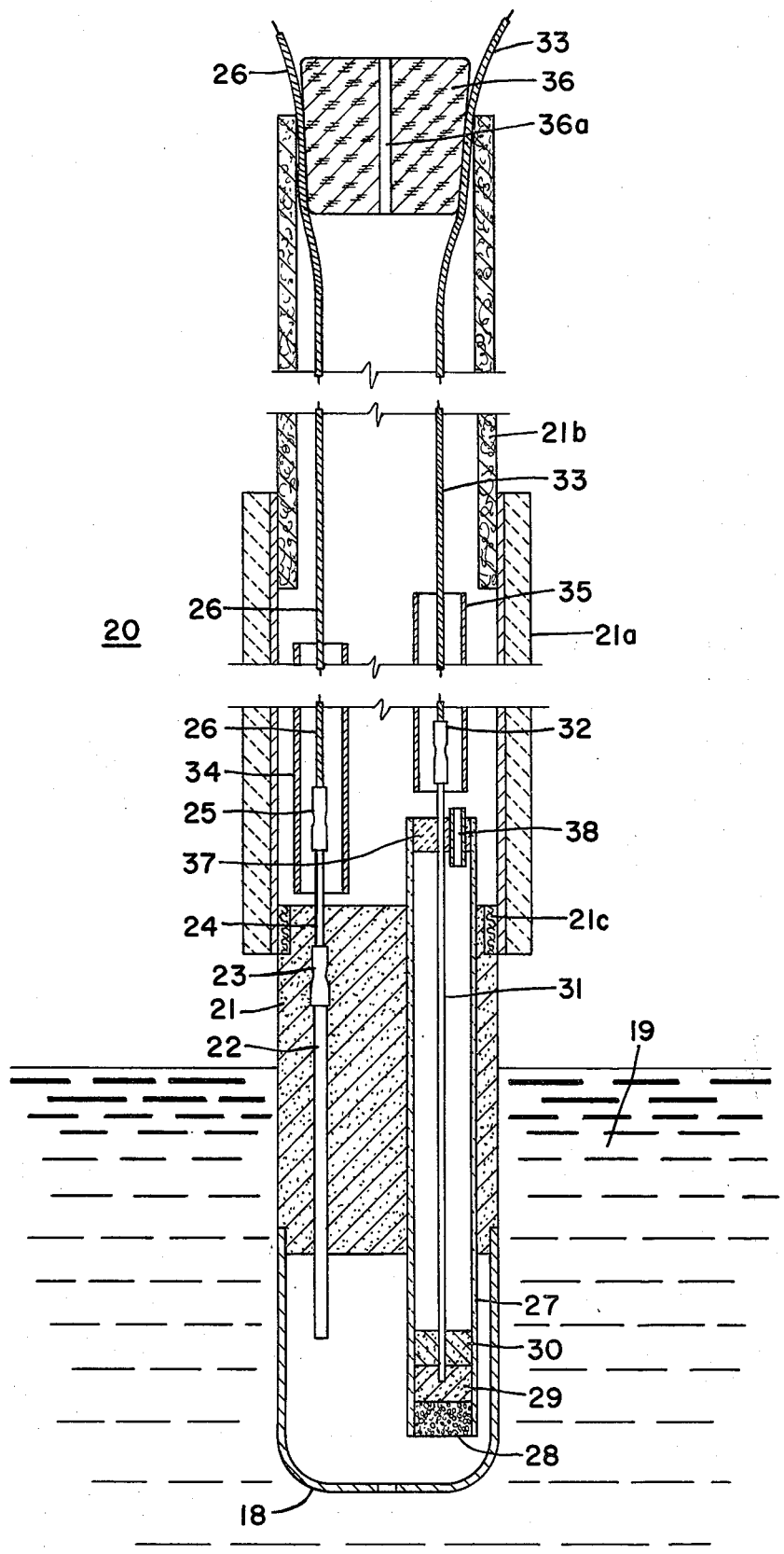
FIG. 3 is a side elevation partly in cross-section showing another modification of an assembly according to applicant's invention.

Applicant's invention as described with reference to the drawings is for an assembly for insertion into a bath to form therewith an electrolytic cell. For illustrative purposes the assemblies will be described as assemblies for determining the concentration of manganese in a bath of molten steel. It is to be understood, however, that the determination of manganese in molten steel is used only for purposes of illustration and is not intended to be limiting. As will be evident to those skilled in the art the invention is applicable to the determination of other materials in molten steel or other molten metal baths or manganese in molten metal baths other than steel.

In the specification the term "immersion end" is intended to mean the end of an assembly or portion thereof which first enters a bath of molten material when inserted therein.

Successful execution of a measurement using an electrolytic cell at elevated temperatures such as that of molten steel will depend on arriving at a suitable cell design, and on selection or development of materials that will withstand the temperature conditions of measurement. In particular, referring to the above schematic cell representation, Table I, the composition of the constituent-responsive material C will be critical.

Material C should have sufficient strength under measurement conditions to act as a partition to keep the molten sample (B) separated from the reference potential producing material (D). It should exhibit no (or only very little) electronic conductance. It should have sufficient ionic conductance to allow making a potentiometer measurement. To obtain good specificity in measuring manganese in the liquid metal phase, that is, to produce a constituent-responsive electrolyte, material C must be capable of entering into a reversible reaction with manganese in metal form in a manner as expressed in the conventionally accepted reaction Equation (1): $Mn_{(conc.\ B)} \rightleftarrows Mn^{++}_{(conc.\ C)} + 2e^-$ A material which can supply divalent manganese ions ($Mn^{+2}$) as required by Equation (1) is considered a good candidate for this essential function. Ideally, there should be no other conducting ions in material C, as these might compete and give rise to interference. In speculation on generalities, however, it is impossible to say whether some other ion, such as an anion or a second cation species would be seriously detrimental. The effect of a competing ion would be nullified, for example, if it does not enter into a reversible electrochemical reaction with a counterpart substance in the sample material, either because no reaction path exists between the two or because the necessary counterpart substance simply is not present in the sample. The molten sample will be of limited range of composition and this factor will help in gaining the needed specificity. Moreover, it is entirely conceivable that a suitable material can be obtained that will show ionic conductance arising uniquely or predominantly from $Mn^{+2}$.

The composition comprising the material C may be either homogeneous or heterogeneous. If homogeneous, its melting point must be sufficiently high to retain its structural configuration at the temperature of measurement, which will be in the range 2900° to 3000°F (1590° to 1650°C) for molten steel.

If a nonhomogeneous composition is used, a constituent-responsive substance of lower melting point may at the temperature of measurement be held as a liquid within the interstices of a porous solid supporting material of high melting point, such as silica, alumina, beryllia, or zirconium silicate. Alternatively the constituent-responsive substance itself may remain essentially in rigid, solid form. Between these extremes, the electroactive material may assume a plastic condition and be disposed within the pores of the porous refractory material, completely filling them or perhaps be disposed only on the surface of the individual refractory particles. In any case an ionic conductive path must be traceable through the material C from interface 2 to interface 3 of the schematically represented electrochemical cell. A porous substance with pores incompletely filled will work as a partition providing the two liquid metal phases do not enter the pores and contact each other. The constituent-responsive material C may take a variety of forms. One suitable configuration is a cylindrical plug held in a plug of refractory material. Another satisfactory form for the material C is a tube closed at one end. Still another satisfactory form for the material C is a quantity disposed in a narrow passageway between opposing walls of refractory material.

Satisfactory electrochemical properties may be obtained by starting with pure silica to which the right amount of a manganese compound is added, and then heating the mixture to give a ceramic like product. In effect a silica-rich, $MnO-SiO_2$ system would be formed. At room temperature such a system would exhibit very high electrical resistance, but at 1600°C its conductivity would become appreciable. Details of construction using this fundamental system are discussed hereinafter.

A cell design for measuring manganese in molten steel is illustrated in FIG. 1. This unit which is arranged in the form of an assembly 10 for insertion in a bath of molten material constitutes an expendable probe suitable for mounting on the end of a manipulator or lance in a manner fully disclosed in the above mentioned U.S. Pat. No. 3,785,947 and the patents to Mead, Moore, and Parker. Since the connector device per se is not applicant's invention it is omitted and only the immersion end is shown in FIGS. 1 and 2. When assembled, the manipulator (not shown) enables the cell to be plunged into a bath of molten metal to effect a measurement.

In FIG. 1 the manganese-responsive material C of the schematically represented cell, Table I, is made in the form of a closed end tube 13. The tube may be cast from the manganese responsive material or a mixture containing manganese responsive material and a refractory material which will remain solid at temperatures higher than the expected cell operating temperature. Alternatively the tube may be of a porous high melting point refractory which has been dipped in molten material containing the manganese responsive material so that interstices of the porous structure will tend to be filled with the manganese responsive material which will solidify therein and remain solid at temperatures below cell operating temperatures. A quantity of metal 14 of known manganese composition is placed inside the tube 13. Metal 14 may be pure manganese or an alloy similar in composition to that of the bath of molten steel. An electronic conductor 16 has an end which makes connection with the metal 14. The other end thereof is electrically connected in a manner not shown to means for establishing an electrical connection with a measuring instrument not shown. A material 15 such as refractory wool packing or a refractory cement may be employed to hold material 14 in place. The open end of the tube 13 may be cemented in an annular groove 11a located in a supporting member 11 of electrically insulating and refractory material. While a body molded from sand is indicated it is to be understood that a ceramic body may be employed or a cup-like structure filled with refractory cement such as that shown in U.S. Pat. No. 3,298,894–R. E. Davies. An electrically conductive element 12, the end of which is located adjacent the outside of tube 13 serves as an electrically (electronic) conductive element of refractory material for contact with the molten bath. It will be connected within the body structure to means for connecting the element to a measuring instrument not shown. A metal cap 18 encloses the space surrounding tube 13 and electrically conductive element 12 to provide protection prior to use and during insertion through the layer of slag which exists on the surface of a bath of molten steel. The cap is held to the support member 11 as by a crimp 11b. The end of support member 11 opposite the immersion end thereof is desirably supported in the end of a tube 17. Tube 17 may be used as a handle for inserting the assembly 10 into a bath of molten material. Alternatively, as shown in the above mentioned Moore patent, the support member 11 may include plug-in electrical connector structure for engagement with mating electrical connector structure carried by a manipulator in which case tube 17 will slide over and protect the immersion end of the manipulator. Tube 17 may be of any suitable material. Thick cardboard tubes and tubes comprised of a thin walled steel tube covered with ceramic impregnated asbestos tape have been found satisfactory.

To make a measurement, the assembly of FIG. 1 is immersed in a molten steel bath 19 as shown in FIG. 2. When this is done the metal cap 18 is destroyed and rapidly disappears in the bath, thereby allowing the molten metal to make contact with the exposed parts of assembly 10, as illustrated in FIG. 2. Temperatures rapidly equilibrate because the parts are kept of small size and mass. The reference metal 14 will melt (m.p. of manganese, 1260°C) thereby making a continuous bridge between the inside of tube 13 and conductor 16. The cell will now have assumed in actuality the structure indicated in the schematically represented cell of Table I. The substances A, B, C, D, and F of Table I correspond respectively to the parts 12, 19, 13, 14, and 16 of FIG. 2. Hence, the e.m.f. readings obtained will indicate the desired manganese content of the molten steel.

An alternative method of probe construction is illustrated in FIG. 3 which shows the assembly during the brief instant after plunging it into the molten metal bath 19 and before the protective cap 18 has been melted away by the bath. In this design the manganese-responsive material is in the form of a pellet 28. The pellet is fastened into the end of an electrically insulating refractory tube 27, the interior of which contains pure manganese reference metal 29 and a conductor 31 which may be of tungsten. The interior of tube 27 of FIG. 3 also contains some manganese silicate 30 to complete the reference electrode structure. A quantity of manganese silicate added to the structure has been found to give more reproducible voltages in actual measurements of manganese in steel.

Pellet 28 may be formed from manganese responsive material or a mixture of manganese responsive material and a refractory material which will remain solid at temperatures higher than the cell operating temperature. Alternatively, the pellet may be of a porous high melting point refractory which has been dipped in molten material containing the manganese responsive material in the same manner as the tube 13 of FIGS. 1 and 2.

Although an MnO—$SiO_2$ pellet composition for the pellet 28 can be formulated and fired to produce a more or less homogeneous vitreous product, which exhibits adequate structural rigidity at the temperature of use along with the desired manganese response, it has been found that superior results are obtained by controlling the $SiO_2$ particle size to avoid complete homogeneity of the product. Thus, if the silica particles are selected of 200 or 350 mesh size for mixture with MnO, the resultant material after firing has low electrical resistivity and exhibits good response to manganese composition. The proportions by weight of ingredients may be taken in the range of 1 to 25% MnO, the balance being silica.

More specifically, pellets 28 are advantageously prepared from a 7.4% weight mixture of manganese monoxide (purified powder, SC 13387, City Chemical Corp.) combined with a good grade of potters sand (325 mesh Supersil, Pennsylvania Pulverizing Company). The presence of a small amount of sodium (about 1%) in the manganese monoxide causes no harm and may be beneficial. The mixture is treated for a period of time in a small porcelain ball mill having quartz pebbles as the grinding medium. The purpose of this treatment is to break down agglomerations, particularly of the manganese monoxide and to insure thorough mixing of the ingredients. If the operation is carried too far, the particle size will be undesirably reduced, and this situation can be determined by microscopic examination of the product, as compared with the startup materials. The powder from the ball mill is prepared for pellet pressing by thoroughly mixing it with a temporary binding material the purpose of which is to enable one to carry out a pellet pressing operation. A number of materials are conventionally available to serve the purpose. It has been found that satisfactory results are obtained if the powder is mixed with some wax emulsion (Nopco 2252L, 11cc/100g powder), some oil (triethanolamine oleate, 8 drops/100g powder), and enough water to make a thick paste. The paste is air dried and the resulting cake is broken into powder. Portions of this powder are weighed out, placed in a steel die, and formed into pellets using considerable pressure in the operation (50,000 psi). After overnight drying of these pellets at 105°C, they are placed in a fused quartz vessel and under hydrogen gas atmosphere are subjected to a furnace heat treatment. The inlet stream of hydrogen should flow through room-temperature water to moderate somewhat the reducing properties of the atmosphere. The furnace temperature is raised in several steps to a maximum of 2350° F. After one-half hour at this temperature the furnace is shut off, and the pellets are allowed to cool with the furnace. The hydrogen atmosphere is continued until the temperature approaches room temperature, at which time the finished pellets are removed.

Probe elements comprised of tube 27 and pellet 28 may be made by fusion sealing pellets inside clear fused quartz tubing of 5mm bore. The pellet may be initially fastened at an intermediate point in a length of tubing somewhat longer than the final element length. A special fixture (provided with a safety shield) is used for the operation, to support the tubing and to maintain a wet hydrogen atmosphere on either side of the pellet. When the tube is removed from the fixture, the excess length is cut off flush with the outer end of the pellet.

Seals formed in this fashion do not have an appealing appearance. Invariably the interface between pellet and tube develops numerous and unavoidable small areas of fracture separation, probably arising from coefficient of expansion differences. This occurrence, however, does not impair later performance, providing the cracking does not proceed all the way through the tube wall. Probe elements with cracked walls should be discarded.

If an air leak develops in the fixture used for sealing in the pellet, the pellet will become dark from oxidation. Elements with darkened pellets should be discarded.

The next step in constructing a probe is to mount the quartz tube 27 with its pellet 28 and a molybdenum rod which constitutes conductive element 22 in a support 21. The molybdenum rod is to make electrical contact with the molten steel. Conductive element 22 is connected to wire 24 which may be of molybdenum of means of crimp connector 23. In a manner known in the arts a sand mixture containing a thermal setting resin binder may be used to making support 21 by placing it with 27 and 22 as inserts in an aluminum mold and forming a sand casting around the two inserts. After removing the casting from the mold, a tungsten wire which serves as electrically conductive element 31 is inserted in the quartz tube 27. Small amounts of manganous silicate 30 as granules (0.2g) and manganese metal 29 as granules (0.25g) are also placed inside the quartz tube 27. These latter materials produce a reference potential. A steel cap 18 covers the protruding rod and reference electrode structure. The cap will protect the element from slag when the immersion end of the assembly is thrust through the slag layer and into the molten steel 19. The cap will melt away rapidly in contact with the steel.

The upper portion of assembly 20, as reduced to practice for gathering data, comprised a length of ceramic covered steel tube 21a into which an under cut end of support 21 wrapped with glass cloth tape 21c was inserted. Tube 21a in turn was a force fit on a cardboard tube 21b thus to form a body structure which could be inserted and withdrawn from a bath of molten material using tube 21b as a handle. As will be evident to those skilled in the arts of expendable immersion pyrometry and the measurement of oxygen in molten steel using an electrolytic cell as taught by the references mentioned above a construction for in plant use will be of the plug-in type immersed by using a manipulator or holder assembly.

Leadwire 24 is connected inside of tube 21a by means of a crimp connector 25 to a leadwire 26 which passes through tubes 21a and 21b for connection to a measuring instrument not shown. A piece of tubular glass cloth insulation 34 is used additionally to furnish electrical insulation and to protect the leadwires 24 and 26 and connector 25 from the heat of the bath. In a similar manner conductor 31 is connected by means of crimp connector 32 to leadwire 33 and the portions of 31 and 33 adjacent the connector are protected by a length of tubular glass cloth 35. A cork stopper 36 with a vent hole 36a was employed to close the tube 21b and hold the leads 26 and 33 in place.

The top end of tube 27 is desirably closed with a quantity of refractory cement 37 through which is passed a length of copper tubing 38 which serves as a vent.

Figure 4:
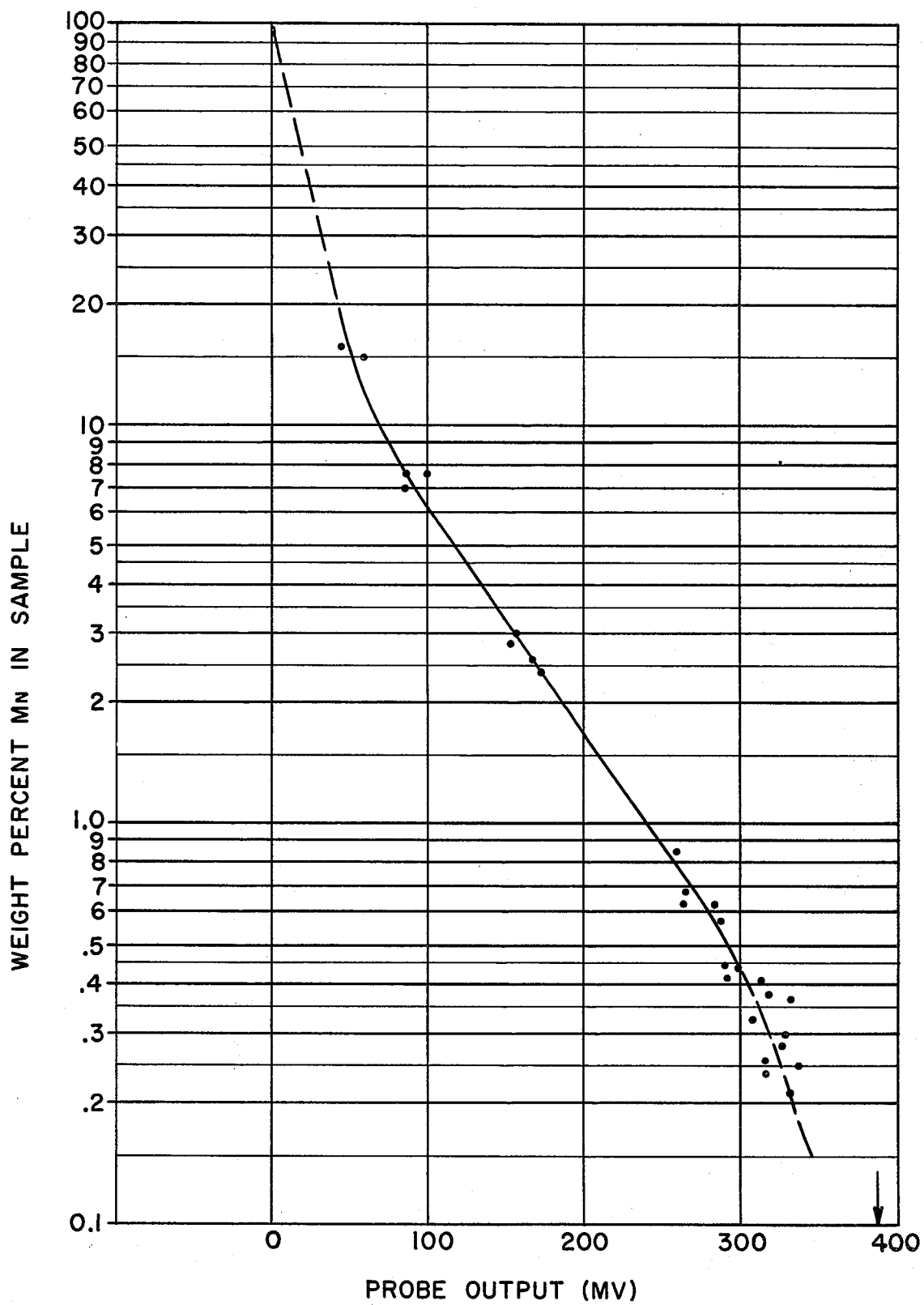
FIG. 4 is a curve usable for the determination of a constituent in a sample in accordance with applicant's invention.

Results obtained with probes of the type shown in FIG. 3 are summarized in FIG. 4 which displays the logarithm of manganese concentration plotted against probe voltage. The points express the individual probe readings. The smooth curve drawn through the points represents an experimentally obtained relationship between probe voltage and manganese concentration. The midportion of the curve of FIG. 4 agrees well with results obtained by chemical analysis of pin samples of the material taken from the test bath and used to plot the points for the curve. The curvature at either end is a result of non-ideal behavior of the system in these regions. These results show that probe voltage correlates with manganese concentration and that manganese concentration can be measured by this technique.

While a mixture of 7.4 weight percent MnO and 92.6 weight percent $SiO_2$ was utilized to form a pellet as above described in detail for purposes of illustration and such pellets were used in assemblies as above described to gather the data used to plot the curve of FIG. 4, many other compositions were also found to be satisfactory for the measurement of manganese in steel. The many compositions included: (0.74gMnO, 7.6g ZnO, 92.6g $SiO_2$); (0.74g MnO, 10g PbO, 92.6g $SiO_2$); (3.7g $Mn_2O_3$, 46.3g $SiO_2$); (0.74g MnO, 4.0g $Na_2CO_3$, 96.0g $SiO_2$); (6.9g $MnSiO_3$, 46.0g Zr $SiO_4$ 270 mesh); (2.0g NaF, 0.37g MnO, 48.0g $SiO_2$); (2.0g NaCl, 0.37g MnO, 48.0g $SiO_2$); (6g $MnSiO_3$, 37g $Al_2O_3$); (3.7g MnO, 0.014g $Fe_2O_3$, 46.3g $SiO_2$); and (0.4g Mn $SiO_3$, 4.0g $K_2SiO_3$, 40.0g Zr $SiO_4$). A mixture of 6.9 grams of $MnSiO_3$ and 46.0 grams of Zr $SiO_4$ (270 mesh) gave better than average results as did a mixture of 6 grams of Mn $SiO_3$ and 37 grams of $Al_2O_3$ (100 mesh).

In addition to making closed end tubes of the type shown in FIGS. 1 and 2 and assemblies as shown in FIG. 3, assemblies were made as shown in FIG. 5.

In the modifications of FIG. 5 an assembly 40 for insertion in a bath of molten material was comprised of a support 41 having an electrically conductive element 42 of molybdenum mounted therein connected to a conductor 44 by a crimp connector 43. Instead of using a tube 27 with a pellet 28 secured therein as in FIG. 3, the assembly of FIG. 5 employed a quartz tube 45 having a flared portion 45a and a tapered quartz plug 46. The plug 46 was secured in the flared portion 45a of tube 45 using a slurry 47 of Mn $SiO_3$ which was permitted to dry after which it was fired to form a bond with the contiguous portions of the plug and tube. The fired and solidified slurry 47 secured in the space of capillary dimensions between the tube and plug provided an ionically conductive constituent-responsive component supported within the equivalent of interstices of a porous supporting material. If desired the mating surfaces of the plug 46 and flared portion 45a of tube 45 may be roughened in the same manner as a ground glass joint to impart a more porous textured surface for reception of the ionically conductive material. The terminology "being supported within interstices or on the surface of particles of a porous supporting component" as used in applicant's claims is intended to include any structure with small or narrow spaces which will support ionically conductive material as taught by applicant.

In the modification of FIG. 5 the pressure of the head of molten steel on the end of plug 46 is in a direction to force the plug into engagement with the flared portion 45a of tube 45 thus to prevent loss of the plug if the ionically conductive material softens or becomes a liquid. This prevents loss of the material of slurry 47. It may be noted here that this feature of the invention is applicable to secure a pellet of solid electrolyte or of a constituent-responsive electrolyte material in accordance with applicant's invention in a tube of refractory material as more fully described in connection with FIGS. 6 and 7.

Still referring to FIG. 5 a quantity of granular Mn metal 48 which served to produce a reference potential was placed inside tube 45. A molybdenum wire 49 with one end immersed in the Mn and the other extending out of the top end of tube 45 provided an electrically conductive element for establishing electrical connection with the Mn and the electrolyte material component in the solidified slurry 47.

The reference number 50 designates a quantity of refractory wool packing to prevent loss of the granular manganese metal 48, and 51 designates a quantity of glass cloth tape wound around support 41 to provide a tight fit between the support and the tube 41a. The tube 41a was employed as a handle for inserting the support and its parts into a bath of molten steel. A cap 52 of mild steel was used to protect 42, 45, 45a, etc., prior to and during insertion of the assembly into a bath.

In FIG. 6 there is shown on an enlarged scale a conical pellet 28' which may be of a conventional solid electrolyte material such as is used in oxygen probes of the type disclosed in the Turkdogan et al. paper or the Baldwin et al. patent or be of an electrolyte material as disclosed in the instant application. This pellet may be secured as by a metal clip 60 of non-interfering materials to hold it in a flared tube 27' of quartz, aluminum oxide or the like. The clip may be a spring clip or if desired a suitable cement such as Duco household cement may be employed to hold the clip 60 or pellet 28' in place as long as such a cement is kept from entering the joint. By means of the clip the pellet 28' is retained in place until insertion of the assembly in a bath of molten material. Upon insertion the head of molten metal will create a force tending to squeeze the pellet in place and the heat of the bath may or may not effect fusion of the pellet to the tube depending upon the materials employed.

In the modification of FIG. 7 a shouldered pellet 28'' is shown inserted in the end of a tube 27''. The pellet may be held in place prior to insertion of the assembly into a bath of molten material by means of a suitable cement 61 such as Ceramabond 503 alumina cement, or by a clip such as clip 60 of FIG. 6.

If carefully sized and shaped, the pellets of either FIG. 6 or FIG. 7 may be retained in place by a friction fit prior to use of the assembly. Upon immersion the head of the molten metal will retain them in place for a measurement.

For the purpose of gathering data as described above, the temperature of the baths of molten steel was kept constant at 2850°F (1566°C). As will be recognized by those skilled in the art it is necessary to know the temperature of the cell components when making concentration measurements with an electrolytic cell in order to correct for the temperature variable. The cell output voltage can be expressed by:

Equation (2): $E = K_1 + K_2 T + K_3 T \log(Mn)_B$ where
$E$ = cell e.m.f.
$T$ = Absolute Temperature, °K
$(Mn)_B$ = Measured manganese activity(concentration)
and $K_1$, $K_2$ and $K_3$ are constants, which can be experimentally determined.

Temperature measuring means may be included as an element of an assembly such as 10, 20, or 40 to be inserted in a bath to form an electrolytic cell, or temperature may be measured using a separate temperature measuring assembly of conventional type. Conventional practice can introduce correction in both temperature terms of Equation 2.

Features of applicant's present invention can be used to measure the concentration of an alkali metal in a molten alloy mixture. A concentration cell of a type similar to one of those described above for manganese measurement may be used, but the constituent responsive electrolyte in this case should be a fused salt comprising a halide of the alkali metal to be determined. Thus fused sodium chloride, or a mixture of sodium chloride and sodium bromide for example can be used to measure sodium concentration, say in a molten bath of sodium-tin alloy. The reference electrode system in this case will be sodium metal or a sodium alloy of constant composition. As has been described, the fused constituent responsive electrolyte can be immobilized within the interstices of an inert solid support material, such as alumina, having a melting point above the melting point of the alloy bath. The resulting probe assembly can be simply inserted in the molten metal bath conveniently to effect the sodium measurement.

Applicant has not only demonstrated that a fired mixture of MnO—SiO$_2$ can be utilized in a solid electrolyte type of structure for the determination of manganese in molten steel but additionally that materials having melting points below the operating temperature of an electrolyte cell can be used to provide an ionically conductive component for an electrolyte material for an assembly insertable in a bath to form an electrolytic cell if the component be supported by electrically non-conductive porous refractory material which remains solid at the operating temperature of the cell. Additionally, applicant has disclosed the mounting of a pellet in a manner to take advantage of the force created by a head of molten material to aid in retaining a pellet in a tube. For these reasons applicant's disclosure of specific examples is not to be construed as limiting the scope of his invention. As will be evident to those skilled in the art one feature may be used without another and still come within the scope of the appended claims.

What is claimed is:

1. An assembly for immersion into a bath of molten steel to form therewith a concentration cell for determining the concentration of manganese in said bath, said assembly comprising body structure capable of withstanding insertion into said bath for a length of time necessary to obtain a measurement, a first electrically conductive element of refractory material having one end protruding from said body structure for contact upon insertion into said bath with said bath and an end thereof inside said body structure electrically connected to means for connecting said element to a measuring instrument, a closed end tubular structure of refractory material projecting from said body structure and having at least a portion of the projecting end of an electrolyte material comprising a fired mixture of an ionically conductive compound of manganese and a porous component of silica, alumina or zirconium silicate, said porous component having a melting point above the temperature of the molten steel and acting as a support for said compound of manganese, a manganese reference material in its liquid state at the operating temperature of said cell contained within said tubular structure in electrically conductive relation with said electrolyte material, a second electrically conductive element extending within said tubular structure and with an end thereof in electrically conductive relation with said reference material and said electrolyte material, the other end of said second electrically conductive element being electrically connected within said body structure to means for connecting said second electrically conductive element to a measuring instrument, and means preventing the ingress of molten steel into said body structure.

2. An assembly according to claim 1 wherein said fired mixture is comprised of 1 to 25 weight percent MnO mixed with SiO$_2$ having particles 200 to 350 mesh size before firing.

3. An assembly according to claim 1 wherein said fired mixture is comprised of 7.4 weight percent MnO and 92.6 weight percent SiO$_2$ before firing.

4. An assembly according to claim 1 wherein said fired mixture is comprised of MnSiO$_3$ and ZrSiO$_4$ before firing.

5. An assembly according to claim 1 wherein said fired mixture is comprised of $MnSiO_3$ and $Al_2O_3$ before firing.

6. An assembly for insertion into a bath of molten steel to form therewith a concentration cell for determining the concentration of manganese in said bath, said assembly comprising body structure capable of withstanding insertion in said bath for a length of time necessary to obtain a measurement, a first electrically conductive element of refractory material having one end protruding from said body structure for contact with said bath upon insertion of said assembly therein and an end thereof inside said body structure electrically connected to means for connecting said element to a measuring instrument, a closed end tubular structure of refractory material projecting from said body structure and having at least a portion of the projecting end comprised of an ionically conductive compound of manganese selected to produce an interfacial voltage with respect to said manganese concentration, said ionically conductive component being held within interstices of a porous supporting component of essentially electrically nonconductive material having a melting point which is above the temperature of molten steel, a manganese reference material including manganous silicate contained within said tubular structure in electrically conductive relation with said electrolyte material, a second electrically conductive element extending within said tubular structure and with an end thereof in electrically conductive relation with said reference material and said electrolyte material, the other end of said second electrically conductive element being electrically connected within said body structure to means for connecting said second electrically conductive element to a measuring instrument, and means preventing the ingress of molten steel into said body structure.

7. An assembly for insertion in a bath of molten material to form therewith an electrochemical cell for determining the concentration of manganese in said bath, said assembly including an electrode structure comprised of means providing a solid partition with at least a part of said partition including manganese responsive material, and a material including manganous silicate contained in said assembly by said partition for establishing a manganese reference potential.

8. An assembly according to claim 7 wherein said at least a part of said solid partition is comprised of a fired mixture of MnO and $SiO_2$.

9. An assembly according to claim 7 wherein said at least a part of said solid partition is comprised of a fired mixture of $MnSiO_3$ and $ZrSiO_4$.

10. An assembly according to claim 7 wherein said at least a part of said partition is comprised of a fired mixture of $MnSiO_3$ and $Al_2O_3$.

* * * * *